United States Patent
Leitner

(10) Patent No.: US 8,005,282 B2
(45) Date of Patent: Aug. 23, 2011

(54) METHOD AND DEVICE FOR PREPARING AN IMPLANT FROM AN IMPLANT MATERIAL

(75) Inventor: Francois Leitner, Uriage (FR)

(73) Assignee: Aesculap AG, Tuttlingen (DE)

( * ) Notice: Subject to any disclaimer, the term of this patent is extended or adjusted under 35 U.S.C. 154(b) by 729 days.

(21) Appl. No.: 12/156,435

(22) Filed: May 30, 2008

(65) Prior Publication Data

US 2008/0304725 A1 Dec. 11, 2008

Related U.S. Application Data

(63) Continuation of application No. PCT/EP2006/068861, filed on Nov. 23, 2006.

(30) Foreign Application Priority Data

Dec. 5, 2005 (DE) .......................... 10 2005 058 760

(51) Int. Cl.
*G06K 9/00* (2006.01)
*A61B 17/56* (2006.01)

(52) U.S. Cl. ........ 382/128; 382/129; 382/130; 600/407; 600/435

(58) Field of Classification Search .................. 382/128, 382/129, 130, 131, 132, 133, 134, 164, 171; 600/407, 435, 437, 439; 378/65, 68, 69; 606/53, 77; 324/309
See application file for complete search history.

(56) References Cited

U.S. PATENT DOCUMENTS

| | | | |
|---|---|---|---|
| 4,575,805 A | 3/1986 | Moermann et al. | |
| 4,615,678 A | 10/1986 | Moermann et al. | |
| 5,204,055 A * | 4/1993 | Sachs et al. | 419/2 |
| 5,340,656 A * | 8/1994 | Sachs et al. | 428/546 |
| 5,726,350 A | 3/1998 | Tsuruta | |
| 5,902,441 A * | 5/1999 | Bredt et al. | 156/284 |
| 6,007,318 A * | 12/1999 | Russell et al. | 425/130 |
| 6,112,109 A | 8/2000 | D'Urso | |
| 6,126,690 A * | 10/2000 | Ateshian et al. | 623/22.4 |
| 6,416,850 B1 * | 7/2002 | Bredt et al. | 428/297.4 |
| 6,459,948 B1 * | 10/2002 | Ateshian et al. | 700/117 |
| 6,640,150 B1 * | 10/2003 | Persson et al. | 700/118 |
| 7,651,701 B2 * | 1/2010 | Meyer et al. | 424/487 |
| 7,799,077 B2 * | 9/2010 | Lang et al. | 623/14.12 |

(Continued)

FOREIGN PATENT DOCUMENTS

| | | |
|---|---|---|
| DE | 39 33 459 | 4/1991 |
| DE | 44 04 695 | 8/1995 |
| DE | 44 21 155 | 12/1995 |
| DE | 199 01 668 | 7/2000 |
| DE | 20 2005 005 085 | 8/2005 |

(Continued)

*Primary Examiner* — Daniel Mariam
*Assistant Examiner* — Nancy Bitar
(74) *Attorney, Agent, or Firm* — Lipsitz & McAllister, LLC

(57) ABSTRACT

A method and device for preparing an implant from an implant material are provided. A defect image of the defect which has a defect contour is made available, in which a first calibration member arranged in or adjacent to the defect is displayed. A second calibration member is arranged on or adjacent to the implant material to be processed, this second calibration member corresponding to the first calibration member. A real-time image of the implant material is displayed on a display device. The defect image is displayed on the display device and superimposed on the real-time image so that the first and the second calibration members are displayed one on top of the other. A processing tool is displayed on the display device in the real-time image and moved over the implant material so that it follows the defect contour displayed in the defect image.

28 Claims, 4 Drawing Sheets

U.S. PATENT DOCUMENTS

| | | |
|---|---|---|
| 2002/0006428 A1 | 1/2002 | Mahmood et al. |
| 2003/0033044 A1 | 2/2003 | Bilyeu |
| 2003/0055502 A1* | 3/2003 | Lang et al. ............... 623/16.11 |
| 2004/0153079 A1 | 8/2004 | Tsougarakis et al. |
| 2004/0254584 A1 | 12/2004 | Sarin et al. |
| 2005/0222574 A1 | 10/2005 | Giordano et al. |
| 2005/0287071 A1* | 12/2005 | Wenz ............................ 424/9.4 |
| 2006/0135719 A1* | 6/2006 | Moszner et al. ........... 526/303.1 |

FOREIGN PATENT DOCUMENTS

| | | |
|---|---|---|
| EP | 0 054 785 | 6/1982 |
| EP | 0 160 797 | 11/1985 |
| EP | 1 426 023 | 6/2004 |
| JP | 2003 126124 | 5/2003 |
| WO | 2004/030528 | 4/2004 |
| WO | 2004/032780 | 4/2004 |
| WO | 2005/077292 | 8/2005 |

* cited by examiner

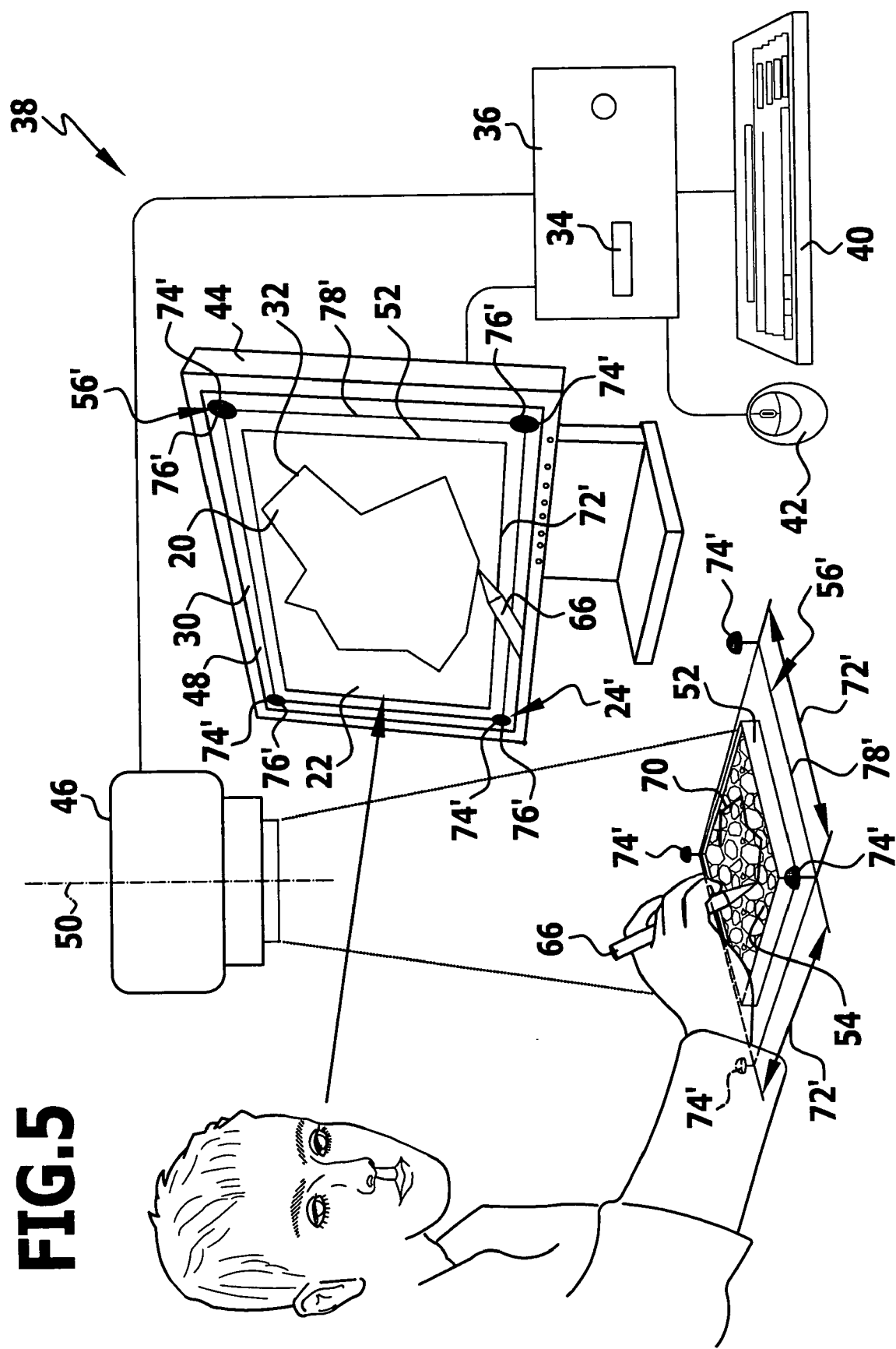

METHOD AND DEVICE FOR PREPARING AN IMPLANT FROM AN IMPLANT MATERIAL

This application is a continuation of International application No. PCT/EP2006/068861 filed on Nov. 23, 2006.

The present disclosure relates to the subject matter disclosed in International application No. PCT/EP2006/068861 of Nov. 23, 2006 and German application No. 10 2005 058 760.7 of Dec. 5, 2005, which are incorporated herein by reference in their entirety and for all purposes.

BACKGROUND OF THE INVENTION

The present invention relates to a method for preparing an implant from an implant material, the implant serving to fill a defect in a human or animal body. Furthermore, the present invention relates to a device for preparing an implant from an implant material, the implant serving to fill a defect in a human or animal body.

Implants which correspond exactly to the shape and the size of a defect are, for example, required for the treatment of cartilage defects resulting from injuries. Implants of this type comprise, for example, a carrier which can be injected with cartilage cells from the patient's own body. A method of the type described at the outset is described, for example, in the German Utility Model No. 20 2005 005 085. However, a navigation system, with the aid of which a defect contour of the defect to be treated is determined with a navigated palpation instrument, is necessary to carry out the known method. This method is complicated and cannot be carried out when a navigation system is not available.

It would therefore be advantageous to provide a method and a device for preparing an implant from an implant material, the implant serving to fill a defect in a human or animal body, which allow the implant to be prepared in a simple manner to fit the defect exactly.

SUMMARY OF THE INVENTION

In accordance with an example embodiment of the present invention, a method for preparing an implant from an implant material is provided in which a defect image of the defect which has a defect contour is made available, in which a first calibration member arranged in or adjacent to the defect is displayed, that a second calibration member is arranged on or adjacent to the implant material to be processed and corresponds to the first calibration member, that a real-time image of the implant material is taken and displayed on a display device in real time, that the defect image made available is displayed on the display device and superimposed on the real-time image in such a manner that the first and the second calibration members are displayed one on top of the other in the same shape and size and that a processing tool is displayed in the real-time image on the display device and moved over the implant material in such a manner that it follows the defect contour displayed in the defect image on the display device.

As a result of the superimposition of the real-time image and the defect image in such a manner that the first and the second calibration members are displayed one on top of the other in the same shape and size, the defect displayed on the display device corresponds to the implant to be prepared from the implant material both in its shape and in its size. If the processing tool is moved over the implant material such that it follows the defect contour displayed in the defect image on the display device, the desired implant can be prepared from the implant material in exactly the size and shape which correspond to the defect. The advantage of this method is to be seen, in particular, in the fact that no navigation system is required. Furthermore, no real-time image of the defect need be available. This means that the method need not be carried out either in an operating theater or by a doctor.

However, it is also eminently suitable for use in an operating theater since only an image generating device for generating the real-time image as well as a display device are required and they can easily be brought into a sterile area. On the other hand, it is not necessary to bring a projector, with which a defect contour can be transferred onto the implant material to be processed, into the sterile area. A calibration member is also to be understood as a calibration structure which is formed from several parts which are in a fixed relationship to one another. Furthermore, the first calibration member can also be a virtual calibration member, i.e., a calibration structure superimposed onto the defect image or a calibration member which corresponds to the second calibration member.

An areal implant is advantageously prepared from an essentially flat implant material. In this way, cartilage implants and also skin implants or the like can be prepared in a desired manner. The method is, therefore, suitable for preparing all types of implants which are suitable for filling a defect in the body.

It is advantageous when a first image generating device with a first optical axis is used for taking the real-time image, the axis being aligned at a first image angle relative to a plane defined by the implant material when a defect image is made available which has been taken with a second image generating device which has a second optical axis, wherein the second optical axis was aligned at a second image angle relative to a plane defined by the defect, and when the first image angle is set in accordance with the second image angle. In this way, it can be ensured that not only the defect in the defect image but also the implant material in the real-time image are displayed on the display device at the same angle. As a result, distortion errors in the representation of the two superimposed images on the display device are avoided and it is ensured that the implant to be prepared exactly fills the defect even with a distorted representation of the defect and the implant material.

In order to avoid distortions during the representation of both the defect and the implant material, it is favorable when the second optical axis was aligned at right angles or essentially at right angles to the plane defined by the defect and when the first optical axis is aligned at right angles or essentially at right angles to the plane defined by the implant material.

In accordance with a preferred variation of the method according to the invention, it may be provided for a defect image to be made available which has been taken by scanning the defect contour with a navigated palpation instrument. Such a defect image has the advantage that on account of its generation by way of navigated scanning of the defect contour itself a scale is known and dimensions of the defect and the defect contour can be ascertained immediately. Furthermore, such a defect image has the advantage that a virtual calibration structure or a virtual calibration member can be superimposed onto the defect image, namely in the correct size scale. If, for example, shape and size of the first calibration member are known, a second calibration member corresponding to it may be superimposed directly onto the defect image and in the correct size scale. As a result, the arrangement of a real calibration member in or on the defect and, therefore, the introduction of a foreign body into a human or animal body is superfluous.

It would be fundamentally conceivable for the defect image to be displayed on the display device as background image. It is, however, advantageous when the real-time image is displayed on the display device as background image and the defect image as foreground image. In both cases, movement of the processing tool can be followed in an optimum manner.

In principle, it would be conceivable for the defect image and the real-time image to be altered only in their size relative to one another so that the two calibration members are displayed in the same size. It is, however, favorable when the defect image and the real-time image are brought into coincidence on the display device by moving the two representations relative to one another and altering an enlarging factor of the two representations relative to one another. In this simple way, the two calibration members can be displayed one on top of the other on the display device so that it can immediately be recognized whether they have the same size and the same position. As a result, it is possible for a scale of the defect image to correspond to a scale of the real-time image so that, without needing to use additional measurement devices, a contour of the defect can be transferred 1:1 onto the implant material.

In principle, it would be conceivable to alter the defect image in size and position such that the two calibration members can be brought into coincidence on top of one another. It is, however, advantageous when the defect image is displayed on the display device unaltered and when the real-time image is moved relative to the defect image and is enlarged or reduced in size in such a manner that the first calibration member and the second calibration member are displayed congruently on the display device. This procedure is particularly simple since the defect image made available need no longer be altered whereas the real-time image, since it is taken directly as the method is being carried out, can easily be altered, for example, also by adjusting an enlarging factor at the first image generating device or altering a position thereof relative to the implant material.

In order to avoid the implant to be prepared not being produced so as to fit the defect exactly, it is favorable when a flat member is used as first and second calibration members, respectively. As a result, any distortions during the superimposition of the representations of the two calibration members on the display device can be avoided.

A disc-shaped member is favorably used. A disc-shaped member has no particularly preferential direction and so the two calibration members can be displayed congruently on the display device during superimposition of the defect image and the real-rime image merely by moving them in two directions at right angles to one another and by adjusting an enlarging factor.

It is advantageous when a calibration structure is used as first and second calibration members, respectively, this structure comprising at least two calibration elements which are in a fixed, geometric relation to one another. This has the advantage, in particular, that the calibration structure can be selected such that no calibration element can or need come directly into contact with the implant material which could hinder the preparation of the implant from the implant material, on the one hand, or also damage the implant material itself.

In order to increase the accuracy of the method, it is favorable when a calibration structure is used which comprises a carrier, on which two, three, four or more calibration members are arranged. In particular, the calibration elements can be arranged at a considerable distance from one another, whereby accuracy during the superimposition of the defect image and the real-time image can be increased.

The real-time image may be generated particularly easily when a digital video camera is used as first image generating device.

In order to be able to process the defect image in a simple manner with a data processing device, it is favorable when a defect image generated with a digital camera is used. This makes it possible to display the defect image directly on the display device and to superimpose it with an additional digital image, for example, the real-time image.

In accordance with a preferred variation of the method according to the invention, it may be provided for the defect image to be taken with the second image generating device prior to the preparation of the implant and for the second calibration member to be arranged in or adjacent to the defect prior to the defect image being taken. In this way, it is possible to generate a desired defect image which is required in order to prepare the desired implant.

In order to avoid a calibration member needing to be moved close to the defect at all, it is favorable when the defect image is taken with the second image generating device prior to the preparation of the implant and when the second calibration member is superimposed onto the defect image in or adjacent to the defect after the defect image has been taken. It is not, therefore, a real but rather a virtual second calibration member which is used, for example, also in the form of a calibration structure. The second calibration member corresponds, on the other hand, to the first calibration member, wherein the second calibration member is selected in shape and size and displayed such that it corresponds to a representation of the first calibration member in the defect image, taking the enlarging scale of the defect image into consideration. The second image generating device can comprise, in particular, a navigation system in conjunction with a navigated palpation instrument, with which a contour, i.e., a defect contour of the defect can be scanned and stored. The data ascertained in this way may be displayed in the form of a defect image, for example, on a screen.

Distortions occurring when taking the defect image and distortions of the defect are avoided when the second image generating device is aligned for taking a defect image in such a manner that its optical axis is aligned at right angles or essentially at right angles to a plane defined by the defect.

A digital camera is advantageously used as second image generating device. This can be connected, for example, to an endoscope so that defect images can also be taken, in particular, from the interior of a human or animal body even during a minimally invasive procedure, for example, within the scope of an arthroscopy of a knee joint.

A processing path corresponding to the defect contour is advantageously drawn onto the implant material with the processing tool. The defect contour is then recognizable on the implant material and the implant to be prepared can be separated from the implant material, for example, by cutting.

The defect contour may be transferred to the implant material particularly easily when a marking pen for marking the processing path on the implant material is used as processing tool. A marking pen is preferably used, with which a contour can be drawn onto the implant without damaging it.

Alternatively, it can also be advantageous when the implant to be prepared is cut out of the implant material with the processing tool. The implant can, therefore, also be prepared without the processing path being marked on the implant material, whereby an additional method step can be saved.

A cutting tool is favorably used as processing tool. As a result, the implant may be separated from the implant material without any problem.

It is favorable when a laser or a scalpel is used as cutting tool. Cutting tools of this type are especially suitable for separating an implant from an implant material.

In order to be able to treat a cartilage defect, for example, in a knee joint in a desired manner, it is favorable when a cartilage replacement implant is prepared from a cartilage replacement implant material with the method. For example, the cartilage replacement implant material can be a carrier material which is injected with autologous chondrocytes which have been grown in the laboratory after previously being removed from the body of the patient.

In addition, in accordance with a further example embodiment of the present invention, a device for preparing an implant from an implant material is provided which comprises an input device for transferring a defect image of the defect which has a defect contour to the device, wherein a first calibration member arranged in or adjacent to the defect is displayed on the defect image, wherein a first image generating device is provided for taking a real-time image of a second calibration member arranged on or adjacent to the implant material to be processed, wherein the first calibration member corresponds to the second calibration member, wherein a display device is provided for displaying and superimposing the real-time image and the defect image, wherein the device is designed in such a manner that the first and the second calibration members can be displayed with the display device one on top of the other in the same shape and size and wherein a processing tool which can be moved along the defect contour displayed in the defect image can, at the same time, be displayed with the display device in real time.

It is possible with the device according to the invention to process an implant material without the aid of a navigation system such that an implant can be prepared which fits the defect to be filled exactly in shape and size.

In accordance with a preferred embodiment of the invention, it may be provided for the device to comprise a data processing device and for the data processing device to be designed to interact with the input device and with the first image generating device. For example, the data processing device can be designed in the form of a computer which can display data on a display device, for example, a monitor. The input device can be designed, in particular, in the form of a reading device for data recording media, for example, in the form of a CD drive or a memory card reading device for memory cards, such as those used, for example, in digital cameras. Alternatively, it would also be conceivable to provide the input device in the form of a digital port on the data processing device in order to read in signals directly from a digital camera.

The data processing device is advantageously designed in such a manner that the defect image and/or the real-time image can be displayed on the display device so as to be alterable in their size and position. For example, the data processing device can be equipped with corresponding software, with which the image processing required for altering size and position of an image can be carried out.

It is favorable when one of the methods according to the invention described above can be carried out with the device.

The following description of a preferred embodiment of an invention serves to explain the invention in greater detail in conjunction with the drawings.

BRIEF DESCRIPTION OF THE DRAWINGS

FIG. 5: shows an additional, schematic illustration of a variation of the method for the processing of the implant material for preparing the desired implant.

DETAILED DESCRIPTION OF THE INVENTION

The method according to the invention described above and the device according to the invention will be explained in greater detail in the follow in conjunction with FIGS. 1 to 4, on the basis of a preferred embodiment.

Figure 1:
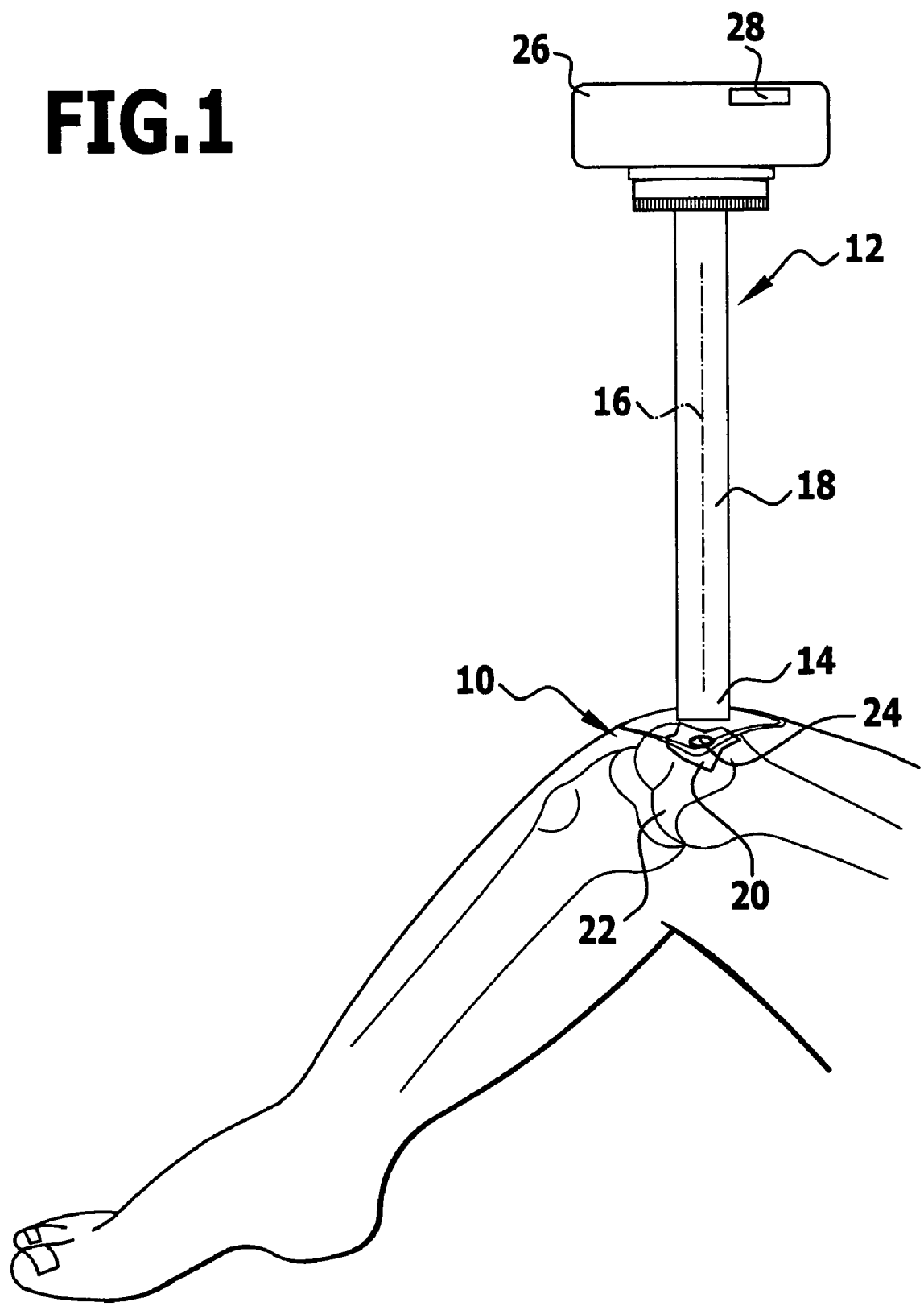
FIG. 1: shows a schematic illustration while a defect image is being taken.

In FIG. 1, an arrangement is illustrated schematically, showing how, within the scope of a minimally invasive procedure, namely in the form of an arthroscopic procedure, a defect image is, for example, taken in a knee joint 10 of a human body. For this purpose, an endoscope 12 is preferably introduced into an open knee joint 10 once the knee joint 10 has been opened up and a shaft 18 of the endoscope 12, which is elongated and defines an optical axis 16, is brought up close to a defect 20 of an articular cartilage 22 with the end 14. Prior to an image of the defect being taken, a calibration member in the form of a flat disc 24 is placed in the defect 20. An image generating device in the form of a digital camera 26 is arranged at the proximal end of the shaft 18 of the endoscope 12, aligned with the optical axis 16 of the shaft 18. Either a light guide which is not illustrated or an optical device which is not illustrated is arranged in the interior of the shaft 18, by means of which it is possible to take a defect image 30 of the defect 20 with the digital camera 26.

Figure 2:
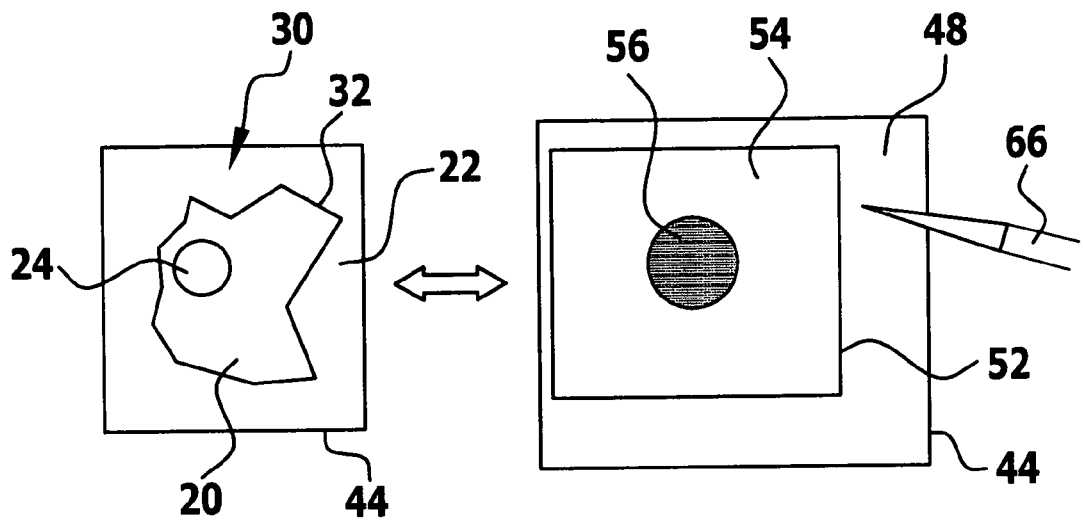
FIG. 2: shows an illustration of an example of a defect image and a real-time image, each with a calibration member.

The defect image 30 is illustrated to the left in FIG. 2 and shows both the defect 20 and also the disc 24 arranged within the defect 20. A defect contour 32, i.e., a boundary line between degenerate cartilaginous tissue and healthy articular cartilage 22 is easy to recognize.

The defect image 30 is stored in a storage device 28 of the digital camera 26, for example, a memory card which can be inserted into a card reading slot 34 of a computer 36 forming a data processing device and from which the stored defect image 30 can then be transferred to the computer 36. The computer 36 is part of a processing device provided altogether with the reference numeral 38 for the preparation of an implant from an implant material. Normally, the computer 36 is connected to a keyboard 40 and a mouse 42, via which an operator can start and operate programs. A screen 44 serving as display device is likewise connected to the computer 36 and serves to display the defect image 30.

In addition, a digital video camera 46 is connected to the computer 36 as additional image generating device, with which a real-time image can be taken and displayed on the screen 44 by means of the computer 36.

For the preparation of an implant which can be inserted into the defect 20 in order to fill this with an exact fit and thus make a regeneration of the damaged cartilaginous tissue possible, the video camera 46 is aligned with its optical axis 50 essentially at right angles to a plane defined by an implant material 54 stored in a flat pan 52. An additional calibration member in the form of a calibration disc 56 is placed on the implant material 54. The calibration disc 56 and the disc 24 are of an identical design, not only in their diameter but also in their height. The real-time image 48 thus generated is displayed on the screen 44, as can be seen in FIG. 2 to the right.

While the real-time image 48 is being taken, attention is paid to the fact that the optical axis 50 is aligned relative to a plane defined by the implant material 54 at the same angle as the optical axis 16 while the defect image 30 is being taken, i.e., in the same way as the optical axis relative to a plane defined by the defect 20. Preferably, the two optical axes 16 and 50 are each aligned at right angles not only to the implant material 54 but also to the defect 20.

Since, during the arrangement of the video camera 46, consideration is not given to the distance, at which it is positioned from the implant material 54, the representations of the defect image 30 and the real-time image 48 do not normally correspond with respect to their size scale. This is shown by the fact that the disc 24 which is identical in shape and size to the calibration disc 56 is displayed differently on the screen 44, namely, as illustrated in FIG. 2 by way of example, smaller.

Figure 3:
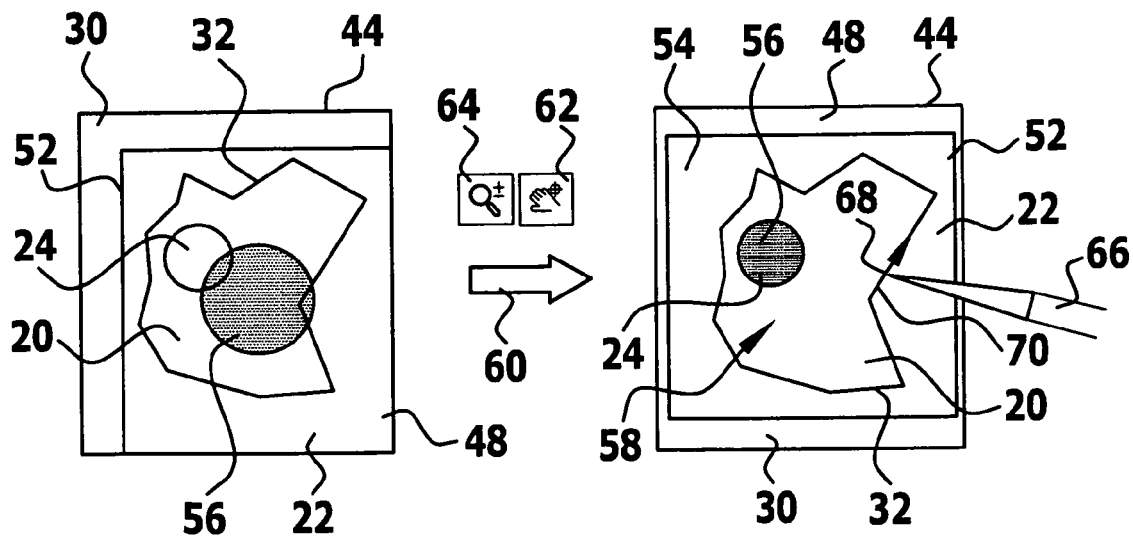
FIG. 3: shows a schematic illustration of the superimposition and calibration of the defect image and the real-time image.
Figure 4:
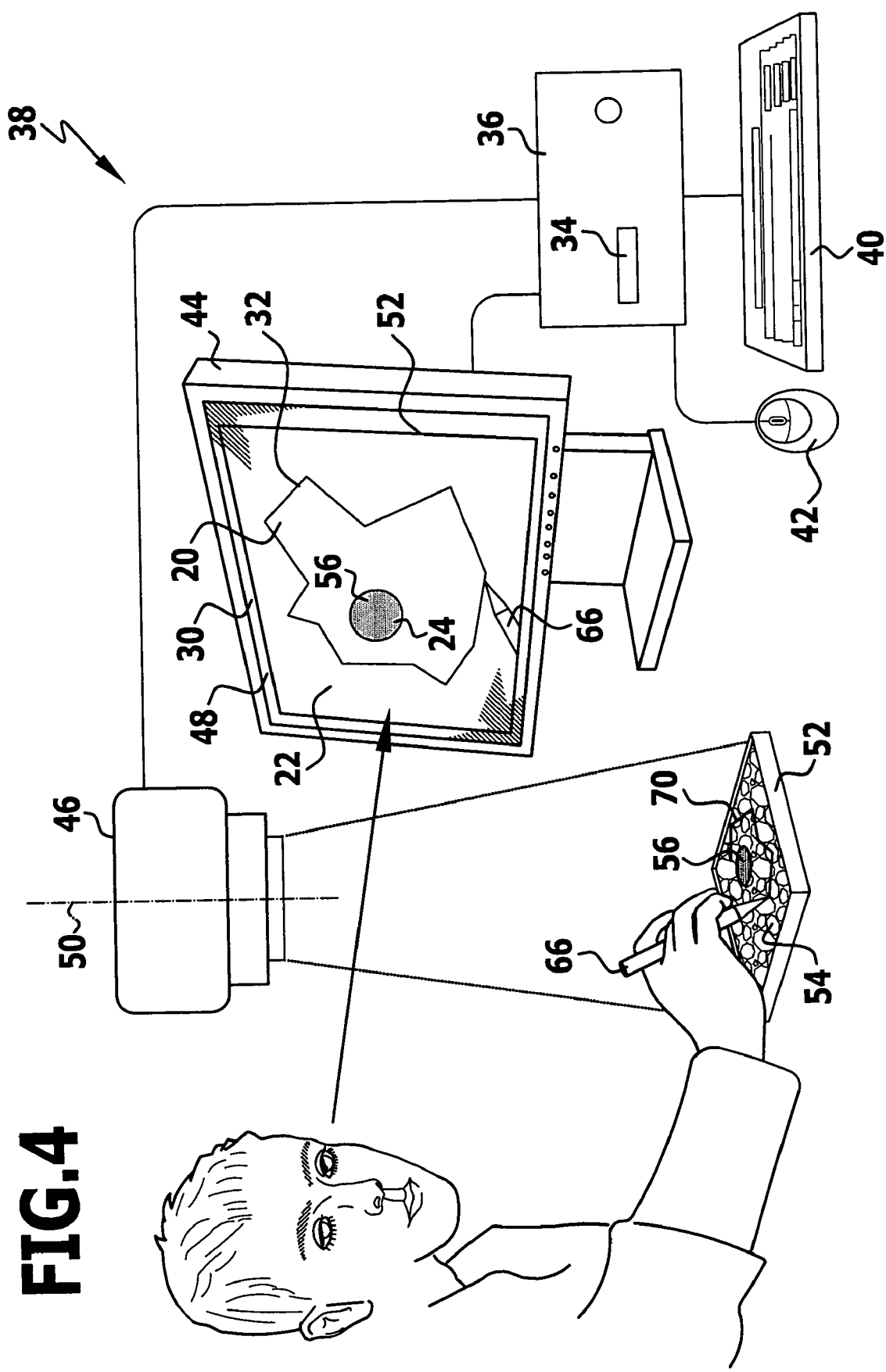
FIG. 4: shows a schematic illustration during the processing of the implant material for preparing the desired implant.

If the defect image 30 and the real-time image 48 are superimposed on the screen 44, as illustrated in FIG. 3 to the left, neither position nor size of the disc 24 and the calibration disc 56 correspond. Whether the real-time image 48 or the defect image 30 are displayed in the foreground or in the background on the screen 44 is, in principle, of no consequence.

In order to prepare an implant 58 which corresponds to the defect 20 in shape and size, the defect image 30 and the real-time image 48 must be adjusted to one another, namely in such a manner that at least the size of the disc 24 corresponds to the size of the calibration disc 56. They need not necessarily overlap. This may, however, be achieved in a particularly simple manner in that the disc 24 and the calibration disc 56 are brought into coincidence. This is carried out by means of an adjusting procedure which is designated symbolically in FIG. 3 by the arrow 60. For example, the real-time image 48 can be moved in two directions at right angles to one another so that, as a result of this displacement 62, the disc 24 is superimposed on the calibration disc 56 on the screen 44 such that their center points are located on top of one another. In addition, as a result of alteration of an enlarging factor 64 of a representation of the real-time image 48 on the screen 44, the size of the calibration disc 56 can be altered such that it corresponds to the size of the disc 24. The adjusting procedure 60 is completed when only one circle formed by the disc 24 and the calibration disc 56 is to be seen on the screen 44. As a result of the adjusting procedure 60, the implant material 54 is displayed on the screen 44 in the same scale as the defect 20.

As a result of the optimized representation of the real-time image 48 and the defect image 30 on the screen 44, as illustrated in FIG. 3, everything is now ready for the preparation of the implant 58 from the implant material 54. For this purpose, a processing tool 66, for example, a marking pen or a scalpel is used. If a marking pen is used, this is moved over the implant material 54 with its tip 86 such that the representation of the processing tool 66 in the real-time image 48 on the screen 44 follows the defect contour 32. A path of movement 70 is thus drawn on the implant material 54 and this corresponds in shape and size to the defect contour 32. For this purpose, either an operator can move the processing tool 66 over the implant material 54 such that the operator moves the tip 68 of the processing tool 66 over the implant material 54 following the defect contour 32 only by looking at the screen 44. Alternatively, a device could also be provided which moves the processing tool 66 over the implant material 54, wherein movement of this device is controlled and regulated as a function of the position of the processing tool 66 in the real-time image 48, namely such that the processing tool 66 always follows the defect contour 32. It would then be possible to prepare the implant 58 completely automatically from the implant material 54.

As already mentioned, the processing tool 66 can also be designed in the form of a cutting tool, for example, a scalpel so that an operator or a correspondingly suitable device can separate the implant 58 from the implant material 54 directly in the manner described.

The method described can be carried out by anybody since it need not necessarily be carried out in an operating theater. If a defect image 30 is made available, the implant 58 can be prepared from the implant material 54 at any optional location.

Alternatively, the adjusting procedure 60 can be carried out such that the real-time image 48 is displayed on the screen 44 unaltered and the defect image 30 is superimposed on the real-time image by way of displacement and adjustment of an enlarging factor for such a time until the disc 24 and the calibration disc 56 are displayed congruently one on top of the other.

In the following, a second variation of the method according to the invention which is modified somewhat in comparison with the method described above will be explained in greater detail in conjunction with FIG. 5, with a second embodiment of a device according to the invention.

The second variation of the method according to the invention differs from the variation described above in that in order to take the defect image no calibration member and also no calibration structure is placed in the defect 20. Instead, a calibration member in the form of a virtual calibration structure 24' is superimposed directly onto the defect image 30 after the defect image 30 has been taken or during the processing of the implant material 54. The calibration structure 24' comprises, in the present case, four solid points arranged in a square. Instead of the calibration disc 56 forming a second calibration member, a real calibration structure 56' is used which is formed by a square frame 78', from which four identical calibration discs 74' protrude out of the plane defined by the frame 78', wherein a side length 72' of the frame 78' has a predetermined value, for example, a length of 10 cm.

The virtual calibration structure 24' is, with a known resolution and a known scaling of the defect image 30, superimposed onto this image in such a manner that four virtual calibration discs 76' arranged in the shape of a square structure are to be seen, their displayed distances in relation to the defect 20 corresponding to the side length 72'. Since an enlarging factor of the defect image 30 need not necessarily correspond to an enlarging factor of the real-time image 48, the actual size of the calibration structure 24' superimposed on the defect image 30 can differ from the size of the calibration structure 56' displayed in the real-time image 48. As a result of corresponding alteration of an enlarging factor 64 of a representation of the real-time image 48 on the screen 44 as well as corresponding alteration of the positions of the real-time image 48 and the defect image 30 relative to one another, the calibration structure 24' can be superimposed on the calibration structure 56' such that only one single calibration structure 24' and 56', respectively, is still visible for an observer. The defect contour 32 is, as already described in conjunction with FIG. 4, transferred virtually on the screen 44 onto the implant material 54 which is prepared with a processing tool 66, the movement of which can be followed in the real-time image 48 displayed on the screen 44 and, therefore, the implant 58 prepared, either by hand or fully automatically.

Alternatively, it is also possible to generate the defect image by scanning the defect contour 32 with a navigated palpation instrument, the movement of which can be traced with a navigation system. This has the advantage, in particular, that no optical image generating device is required for taking the defect image and, in addition, the calibration structure 24' can be superimposed virtually onto the defect image 30 in the correct scale since the enlarging scale can also be ascertained and made available immediately by a navigation system during the navigated scanning of the defect contour 32.

What is claimed is:

1. A method for preparing an implant from an implant material, said implant serving to fill a defect in a human or animal body, comprising:
   making available a defect image of the defect having a defect contour, with a first calibration member arranged in or adjacent to the defect being displayed in said image,
   arranging a second calibration member on or adjacent to the implant material to be processed, said second calibration member corresponding to the first calibration member,
   taking and displaying a real-time image of the implant material in real time on a display device,
   displaying the defect image on the display device superimposed on the real-time image in such a manner that the first and the second calibration members are displayed one on top of the other in the same shape and size,
   displaying a processing tool in the real-time image on the display device and moving the processing tool over the implant material in such a manner that it follows the defect contour displayed in the defect image on the display device, and
   preparing the implant material for the production of an implant in exactly the same size and shape which corresponds to the defect.

2. The method of claim 1, wherein an areal implant is prepared from an essentially flat implant material.

3. The method of claim 1, wherein:
   a first image generating device with a first optical axis is used for taking the real-time image, said axis being aligned at a first image angle relative to a plane defined by the implant material,
   said defect image is taken with a second image generating device having a second optical axis, wherein the second optical axis was aligned at a second image angle relative to a plane defined by the defect, and
   the first image angle is set in accordance with the second image angle.

4. The method of claim 3, wherein the second optical axis was aligned at right angles or essentially at right angles to the plane defined by the defect and wherein the first optical axis is aligned at right angles or essentially at right angles to the plane defined by the implant material.

5. The method of claim 1, wherein a said defect image is taken by scanning the defect contour with a navigated palpation instrument.

6. The method of claim 1, wherein the real-time image is displayed on the display device as a background image and the defect image is displayed as a foreground image.

7. The method of claim 1, wherein the defect image and the real-time image are brought into coincidence on the display device by moving the two representations relative to one another and altering an enlarging factor of the two representations relative to one another.

8. The method of claim 7, wherein the defect image is displayed on the display device unaltered and wherein the real-time image is moved and enlarged or reduced in size relative to the defect image in such a manner that the first calibration member and the second calibration member are displayed congruently on the display device.

9. The method of claim 1, wherein a flat member is used as the first and second calibration members, respectively.

10. The method of claim 9, wherein said flat member comprises a disc-shaped member.

11. The method of claim 1, wherein a calibration structure is used as the first and second calibration members, respectively, said structure comprising two calibration elements in a fixed, geometric relation to one another.

12. The method of claim 11, wherein said calibration structure comprises a carrier with at least two calibration elements being arranged thereon.

13. The method of claim 3, wherein a digital video camera is used as the first image generating device.

14. The method of claim 3, wherein the defect image is generated with a digital camera.

15. The method of claim 3, wherein:
   prior to the preparation of the implant the defect image is taken with the second image generating device, and
   prior to the defect image being taken the second calibration member is arranged in or adjacent to the defect.

16. The method of claim 3, wherein:
   prior to the preparation of the implant the defect image is taken with the second image generating device, and
   after the defect image has been taken the second calibration member is superimposed onto the defect image in or adjacent to the defect.

17. The method of claim 15, wherein in order to take the defect image the second image generating device is aligned in such a manner that its optical axis is aligned at right angles or essentially at right angles to a plane defined by the defect.

18. The method of claim 3, wherein a digital camera is used as second image generating device.

19. The method of claim 1, wherein a processing path corresponding to the defect contour is drawn onto the implant material with the processing tool.

20. The method of claim 19, wherein a marking pen for marking the processing path on the implant material is used as the processing tool.

21. The method of claim 1, wherein the implant to be prepared is cut out of the implant material with the processing tool.

22. The method of claim 21, wherein a cutting tool is used as the processing tool.

23. The method of claim 22, wherein a laser or a scalpel is used as the cutting tool.

24. The method of claim 1, wherein a cartilage replacement implant is prepared from a cartilage replacement implant material.

25. A device for preparing an implant from an implant material, said implant serving to fill a defect in a human or animal body, comprising:
   an input device for transferring a defect image to the device, said defect having a defect contour, wherein a first calibration member arranged in or adjacent to the defect is displayed on the defect image,
   a first image generating device for taking a real-time image of a second calibration member arranged on or adjacent to the implant material to be processed, the first calibration member corresponding to the second calibration member, a display device for displaying and superimposing the real-time image and the defect image, the device being designed in such a manner that the first and the second calibration members are displayed with the display device one on top of the other in the same shape and size, and a processing device including a processing tool movable along the defect contour displayed in the defect image is adapted to be such that the processing tool is displayed with the display device in real time at the same time the defect image is displayed.

26. The device of claim 25, comprising a data processing device designed to interact with the input device and with the first image generating device.

27. The device of claim 26, wherein the data processing device is designed in such a manner that the defect image and/or the real-time image are adapted to be displayed on the display device so as to be alterable in their size and position.

28. The device of claim 25, adapted to carry out a method for preparing an implant from an implant material, said implant serving to fill a defect in a human or animal body, wherein:

a defect image of the defect having a defect contour is made available, a first calibration member is arranged in or adjacent to the defect being displayed in said defect image, a second calibration member is arranged on or adjacent to the implant material to be processed, said second calibration member corresponding to the first calibration member, a real-time image of the implant material is taken and displayed in real time on a display device, the defect image is displayed on the display device and superimposed on the real-time image in such a manner that the first and the second calibration members are displayed one on top of the other in the same shape and size, and a processing tool is displayed in the real-time image on the display device and moved over the implant material in such a manner that it follows the defect contour displayed in the defect image on the display device.

* * * * *